United States Patent
Kim

(10) Patent No.: US 12,042,424 B2
(45) Date of Patent: Jul. 23, 2024

(54) THUMB SUCTIONING PREVENTION BRACE

(71) Applicant: SILLYMANN CO., LTD., Paju-si (KR)

(72) Inventor: ChangHo Kim, Seoul (KR)

(73) Assignee: SILLYMANN CO., LTD., Paju-si (KR)

( * ) Notice: Subject to any disclaimer, the term of this patent is extended or adjusted under 35 U.S.C. 154(b) by 175 days.

(21) Appl. No.: 17/725,555

(22) Filed: Apr. 21, 2022

(65) Prior Publication Data

US 2022/0339025 A1  Oct. 27, 2022

(30) Foreign Application Priority Data

Apr. 27, 2021  (KR) .......................... 20-2021-0001321

(51) Int. Cl.
  *A61F 5/00* (2006.01)
  *A61F 5/50* (2006.01)

(52) U.S. Cl.
  CPC ..................................... *A61F 5/50* (2013.01)

(58) Field of Classification Search
  CPC ...... A61F 5/50; A61F 5/05875; A61F 5/5866; A61F 5/10; A61F 5/11; A61F 13/105; A45D 29/00; A45D 2029/008; A45D 19/0051; A45D 19/0086; A45D 19/01517; A41D 13/087
  USPC ........................................................ 128/880
  See application file for complete search history.

(56) References Cited

U.S. PATENT DOCUMENTS

| | | | | |
|---|---|---|---|---|
| 2,225,896 | A | * | 12/1940 | Belknap ..................... A61F 5/50 128/880 |
| 4,984,592 | A | * | 1/1991 | Hellein ................... A45D 44/12 2/21 |
| 5,181,914 | A | * | 1/1993 | Zook ...................... A61F 13/105 128/893 |
| 6,012,165 | A | * | 1/2000 | Cain ...................... A41D 13/087 2/21 |
| 9,591,881 | B1 | * | 3/2017 | Sarkissian ............ A41D 19/001 |
| 2013/0327344 | A1 | * | 12/2013 | Zilber ........................ A61F 5/50 128/880 |
| 2017/0188683 | A1 | * | 7/2017 | Davis ............... A41D 19/01511 |

FOREIGN PATENT DOCUMENTS

| KR | 10-2016-0057090 A | 5/2016 |
|---|---|---|
| KR | 10-2016-0147395 A | 12/2016 |
| KR | 10-1925517 B1 | 12/2018 |

* cited by examiner

*Primary Examiner* — Adam Baker
(74) *Attorney, Agent, or Firm* — Park, Kim & Suh, LLC

(57) ABSTRACT

A thumb suctioning prevention brace according to the inventive concept includes a body surrounding opposite sides, a back portion, and a nail of a thumb and having an opening formed therein so that a bottom portion of the thumb is exposed, a band part coupled to a lower portion of the body and fixed to a wrist by connecting opposite ends thereof, and a detachable part provided inside an upper portion of the body, a specific design being displayed on an outer peripheral surface thereof, wherein the body is made of a transparent material, and the specific design is exposed instead of the nail. The effect of the inventive concept is to provide a thumb suctioning prevention brace capable of correcting a habit of suctioning a thumb by recognizing, through the specific design, the infant that a thumb suctioning behavior is uncomfortable.

11 Claims, 8 Drawing Sheets

THUMB SUCTIONING PREVENTION BRACE

CROSS-REFERENCE TO RELATED APPLICATIONS

A claim for priority under 35 U.S.C. § 119 is made to Korean Utility Model Application No. 20-2021-0001321 filed on Apr. 27, 2021, in the Korean Intellectual Property Office, the entire contents of which are hereby incorporated by reference.

BACKGROUND

Embodiments of the inventive concept described herein relate a thumb suctioning prevention brace.

In general, infants have a habit of suctioning fingers thereof even though there is some difference therebetween, and studies have reported that the suctioning of fingers is a habit occurring in about 40% of one-year-old infants, about 20% of five-year-old infants, and about 5% of 10-year-old children.

Further, the habit of suctioning fingers gradually disappears over time, but in some cases, the habit continues until late. In this case, it is known that the habit of suctioning fingers may cause deformities of a jawbone and teeth, interfere with chewing food and breathing, and in severe cases, may cause damage to a face shape.

Meanwhile, the infants experience joy, warmth, satisfaction, and comfort without tension through suctioning fingers, and in most cases, suction fingers to resolve various complaints, for example, when the infants feel fear, feel hungry, feel sleepy, and feel uncomfortable.

Thus, when the suctioning of fingers is excessively limited, the infants may be psychologically and adversely affected. Thus, careful consideration is required so that various side effects as described above are not caused as the suctioning of fingers continues without psychologically affecting the infants.

In order to prevent such a habit of suctioning fingers, a number of finger suctioning prevention braces have been developed.

However, a brace according to the related art is formed to simply surround the thumb of an infant, the brace is suctioned instead of fingers, and thus the suctioning habit is merely corrected. However, there is inconvenience in that education not to suction thumbs is performed only verbally.

Further, since the brace according to the related art is made of a soft material such as silicone but is fixed to a wrist using a band and is not stretched, the thumb cannot be freely bent, and thus there is inconvenience in that the infants cannot grip an object.

Moreover, one side of the brace is open so that air may pass through the thumb in a state in which the brace according to the related art is worn, but the thumb is extracted and is eventually suctioned. Further, as air pass through the open part, when the brace is worn, the infants cannot immediately feel joy, warmth, satisfaction, and comfort without tension that are felt by suctioning the thumb, and rather than feel anxious and uncomfortable, and thus the infants refuse to wear the brace.

Further, the brace according to the related art is worn on the thumb and is provided with a band to be fixed to the thumb. As the brace and the band are integrally configured, when the band is pulled, the brace itself moves, and when the band is cut, a new product should be purchased.

SUMMARY

Embodiments of the inventive concept provide a thumb suctioning prevention brace in which a detachable part having a specific design displayed thereon is provided inside an upper portion of a body, the specific design instead of a nail of an infant is exposed through the transparent body, the infant is recognized that a thumb suctioning behavior is uncomfortable through the specific design, and thus a habit of suctioning a thumb may be corrected.

Embodiments of the inventive concept also provide a thumb suctioning prevention brace in which the detachable part is attached to and detached from the body in an interchangeable manner, whereby various specific designs are recognized by the infant, and of course, the infant may be recognized not to suction the thumb by telling different stories according to the designs displayed on the detachable part.

Embodiments of the inventive concept also provide a thumb suctioning prevention brace in which bent holes are formed in a middle part of the body to be long in a width direction and a plurality of connection parts are formed so that only a portion of a tip of the thumb is opened through an opening, whereby the thumb is supported by the connection parts when the infant bends the thumb, the bent holes are widened, and thus the infant may easily bend the thumb and easily grip an object.

According to an exemplary embodiment, a thumb suctioning prevention brace includes a body surrounding opposite sides, a back portion, and a nail of a thumb and having an opening formed therein so that a bottom portion of the thumb is exposed, a band part coupled to a lower portion of the body and fixed to a wrist by connecting opposite ends thereof, and a detachable part provided inside an upper portion of the body, a specific design being displayed on an outer peripheral surface thereof, wherein the body is made of a transparent material, and the specific design is exposed instead of the nail.

Further, the body may have fitting holes formed therein to pass through opposite sides of an upper portion thereof and have a contact groove which is inserted into an upper inner side thereof and with which the detachable part is in close contact, and the detachable part may include fitting bosses fitted and coupled to the fitting holes on opposite sides thereof and locking bosses protruding outward from ends of the fitting bosses and caught on an outer surface of the body, and the outer peripheral surface of the detachable part may be in close contact with and is fixed to the contact groove.

Further, the body may have one or more connection parts connecting opposite ends of the opening and a plurality of bent holes that pass long in a widthwise direction thereof and are formed in a lengthwise direction thereof, the connection parts may be formed at locations corresponding to a tip of the thumb so that the thumb is not extracted through an upper portion of the opening, and when the thumb is bent, the tip of the thumb may be supported by the connection parts, the bent holes may be widened in a lengthwise direction thereof, and as the thumb is bent, the body may be integrally bent.

Further, the detachable part may have a concave groove surrounding the nail, and a line may protrude from an inner peripheral surface of the concave groove in a lengthwise direction of the body, and the line may space the nail apart from the concave groove, may be provided as a plurality of lines spaced apart from each other in a widthwise direction thereof, and thus may form a passage through which foreign substances flow.

Further, the bent holes may be formed at locations that are below the connection parts and correspond to a first joint of the thumb, and when an upper outer periphery surface of the body is suctioned, the bent holes may be not inserted into a mouth, and thus the body may be suctioned while forming a vacuum state.

Further, the body may have a plurality of fixing rings having insertion holes formed outside a lower portion thereof, the band part may include a bendable intermediate band inserted into the fixing rings, a fastener formed at one end of the intermediate band and forcibly fitted in the insertion holes, and a fastening band extending from the other end of the intermediate band and having a plurality of fastening holes in which the fastener is forcibly fitted, and as the intermediate band is fixed to the fixing rings and is moved along the insertion holes, when the fastener is fastened to the fastening holes, the fastener and the fastening hole may be selectively located and fastened in any one portion of a circumference of the wrist.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
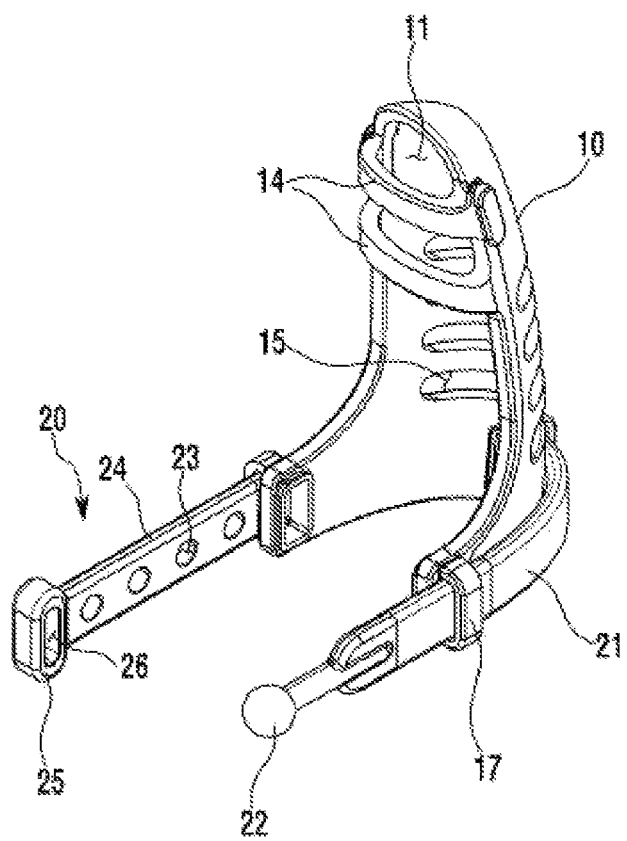
FIG. 1 is a perspective view illustrating a thumb suctioning prevention brace according to an embodiment of the inventive concept.

Advantages and features of the inventive concept and a method of achieving the advantages and the features will become apparent with reference to embodiments described below in detail together with the accompanying drawings. However, the inventive concept is not limited to the embodiments described below but may be implemented in various forms, and the present embodiments merely make the disclosure of the inventive concept complete and are provided to completely inform the scope of the inventive concept to those skilled in the art to which the inventive concept belongs, and the inventive concept is merely defined by the scope of the appended claims. Throughout the specification, the same reference numerals refer to the same components.

Hereinafter, the inventive concept will be described with reference to the accompanying drawings for describing a thumb suctioning prevention brace according to the embodiments of the inventive concept.

Figure 2:
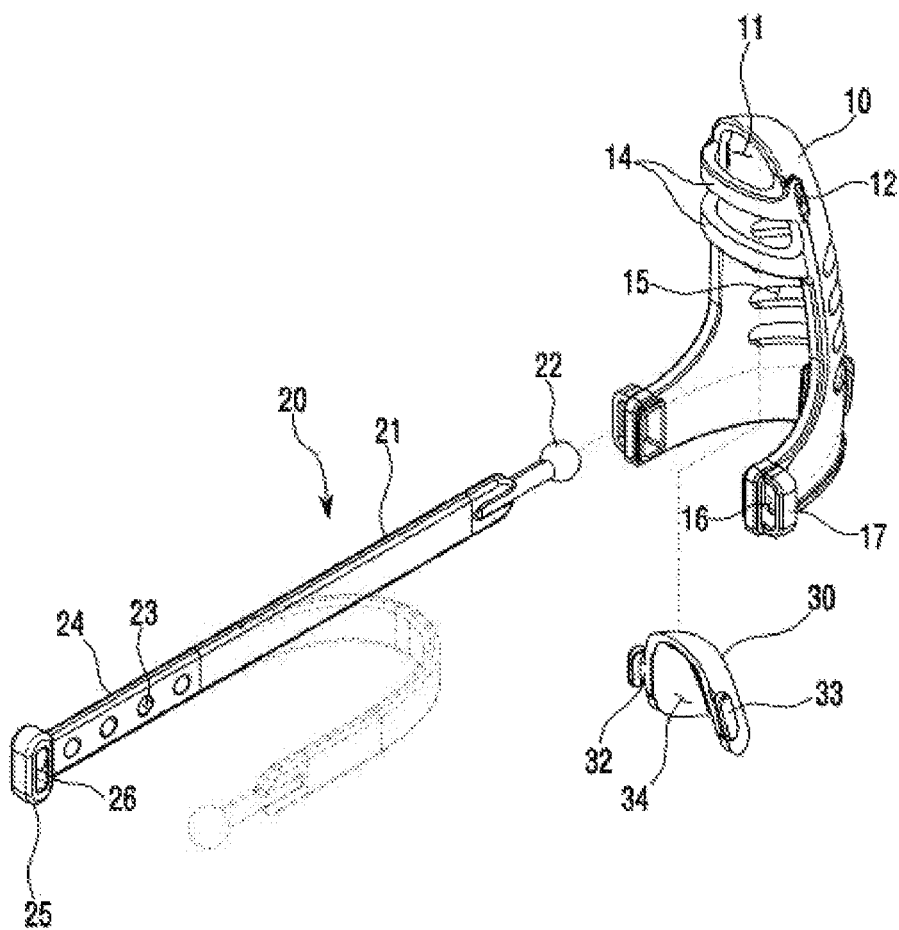
FIGS. 2 and 3 are exploded perspective views illustrating the thumb suctioning prevention brace according to an embodiment of the inventive concept.
Figure 3:
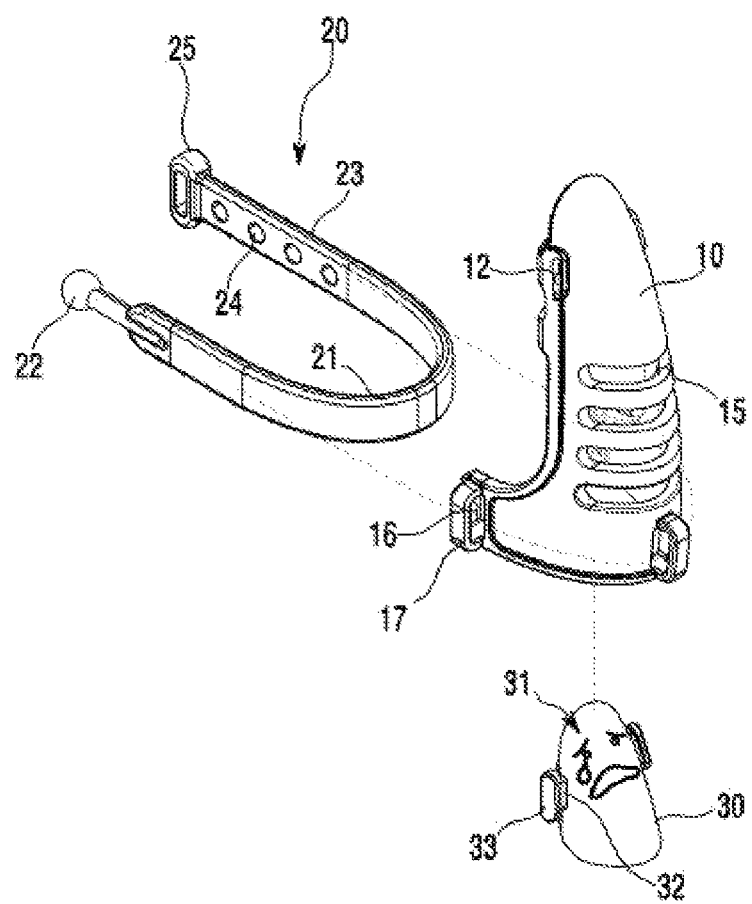
Figure 4:
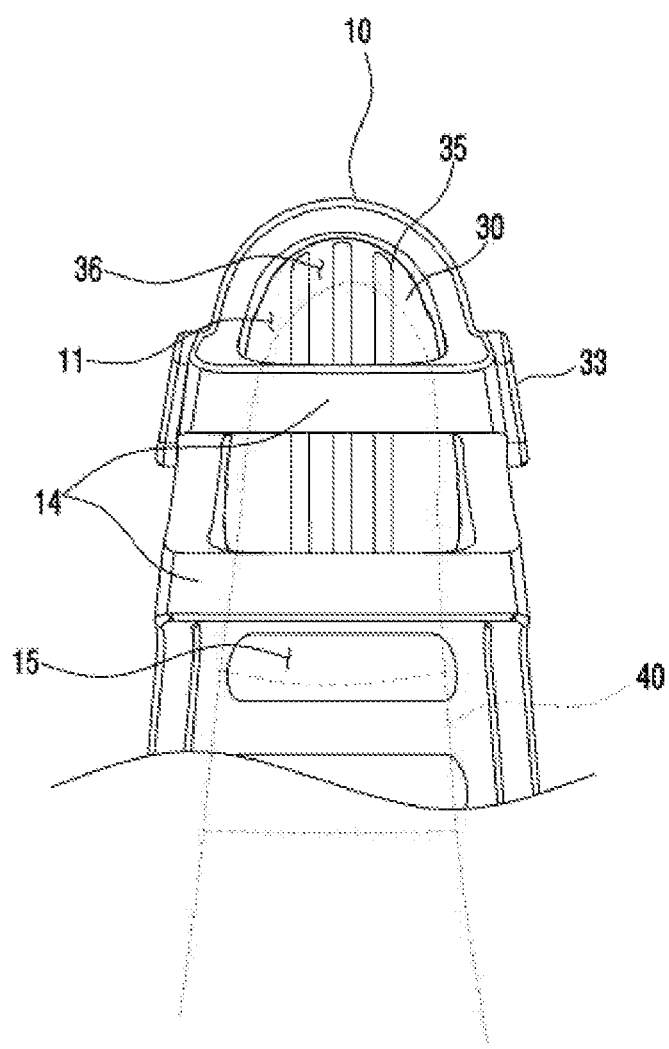
FIG. 4 is a front view illustrating the thumb suctioning prevention brace according to an embodiment of the inventive concept.
Figure 5:
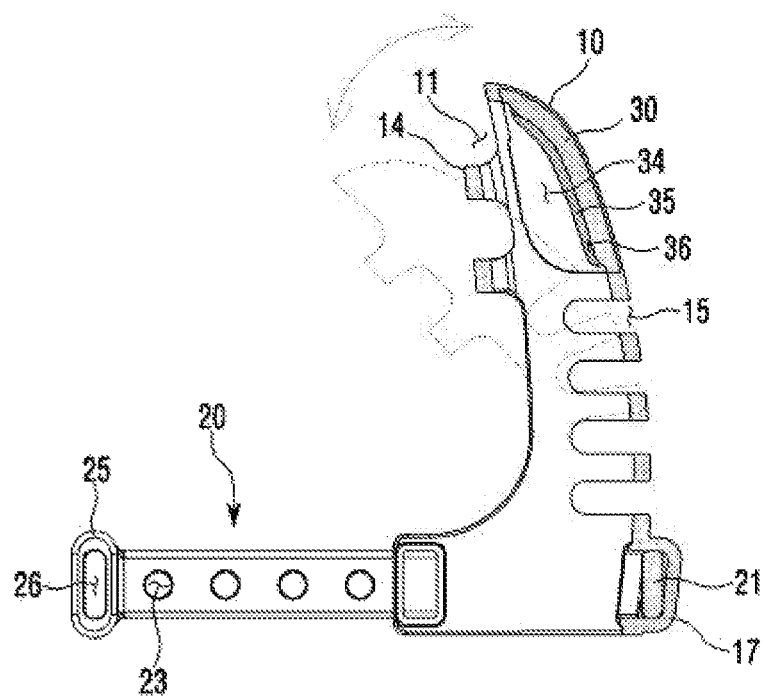
FIGS. 5 and 6 are side cross-sectional views illustrating the thumb suctioning prevention brace according to an embodiment of the inventive concept.
Figure 6:
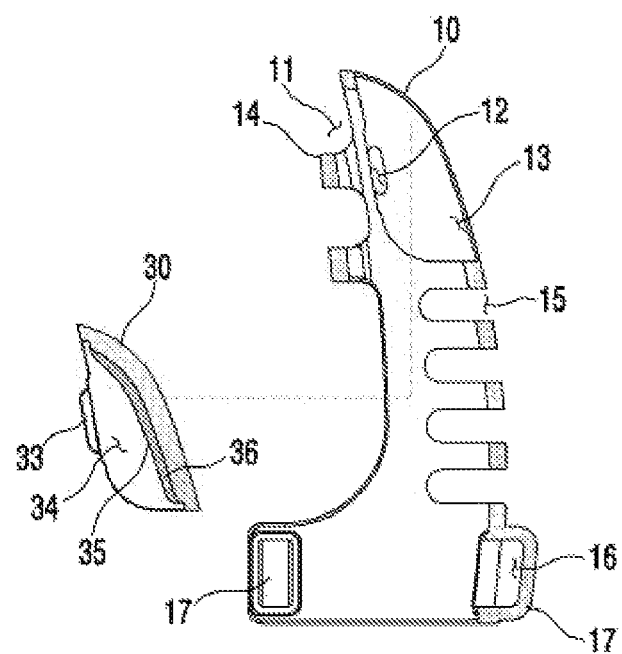
Figure 7:
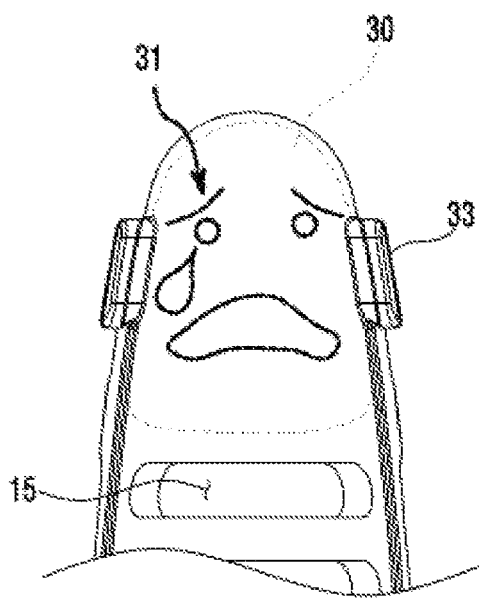
FIG. 7 is a rear view illustrating a state in which a specific design of the thumb suctioning prevention brace is transmitted and displayed according to the embodiment of the inventive concept.
Figure 8:
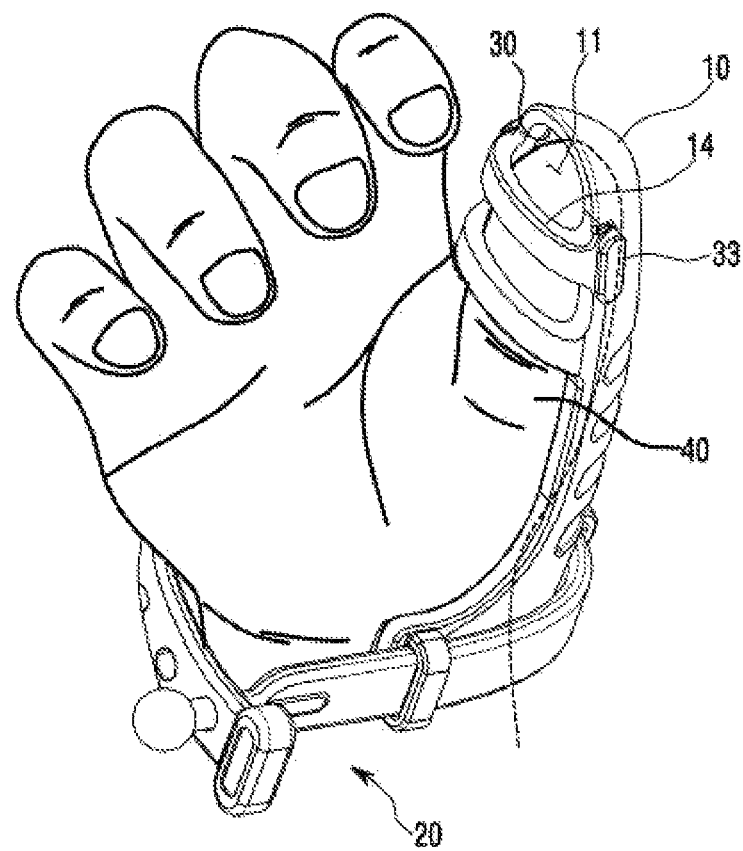
FIG. 8 is an exemplary view illustrating a state in which the thumb suctioning prevention brace is worn according to the embodiment of the inventive concept.

Referring to FIGS. 1 to 3, the thumb suctioning prevention brace according to the inventive concept includes a body 10, a band part 20, and a detachable part 30.

First, the body 10 covers opposite sides, a back portion, and a nail of a thumb 40, and has an opening 11 formed therein so that a bottom portion of the thumb 40 is exposed.

That is, a space into which the thumb 40 may be inserted is formed inside the body 10, and the bottom portion of the thumb 40 is exposed through the opening 11.

Further, the body 10 has fitting holes 12 therein to pass through opposite sides of an upper portion thereof and has a contact groove 13 which is inserted into an upper inner side thereof and with which the detachable part 30 is in close contact. In this case, the contact groove 13 is detachably provided with the detachable part 30, which will be described below, to be in close contact with the detachable part 30.

Further, the body 10 has one or more connection parts 14 connecting opposite ends of the opening 11. Here, the plurality of connection parts 14 may be formed to be spaced apart from each other in a lengthwise direction of the body 10 and may be formed only at locations corresponding to a tip of the thumb 40.

That is, the connection parts 14 are formed at the locations corresponding to the tip of the thumb 40 so that the thumb 40 is not extracted through an upper portion of the opening 11.

In particular, referring to FIGS. 4 to 7, the connection part 14 is formed at a location corresponding to an upper middle portion of the tip of the thumb 40 so that only an upper portion of the tip of the thumb 40 may be exposed through the opening 11. Here, when the connection part 14 is formed in a middle portion of the tip of the thumb 40 or in a portion below the middle portion thereof, the tip may be bent, and thus a user may easily grip an object. However, the tip of the thumb 40 extracted through the opening 11 is suctioned, and this makes it impossible to achieve the purpose of the inventive concept.

Accordingly, since the connection part 14 is formed in an uppermost of the opening 11 and only a portion of the tip of the thumb 40 is exposed, it is preferable that the thumb 40 is not extracted through the opening 11, but the inventive concept is not limited thereto.

Further, when the thumb 40 is bent, as a bottom portion of the tip of the thumb 40 is supported, the connection part 14 may allow the user to grip an object.

Further, in the body 10, a plurality of bent holes 15 that pass long in a widthwise direction thereof are formed in the lengthwise direction thereof. In this case, the bent holes 15 may pass such that the opposite sides and the back portion of the thumb 40 are opened, and thus may be easily widened when the body 10 is bent and may be ventilated.

Moreover, in order to further facilitate the bending of the bent holes 15, a widthwise length of the formed bent holes 15 may be formed to be longer toward a lower portion of the body 10.

As the connection parts 14 and the bent holes 15 are formed, in the body 10, when an infant bends the thumb 40, the tip of the thumb 40 is supported by the connection parts 14, the bent holes 15 are widened in a lengthwise direction by a bending force, and as the thumb 40 is bent, the body 10 is integrally bent.

Thus, while wearing the inventive concept, the infant may easily bend the thumb 40, grip an object, at the same time, prevent the thumb 40 from being separated from the body 10, and thus suction the body 10 instead of the thumb 40, and thus the suctioning habit may be corrected.

Meanwhile, when the infant suctions the thumb 40, as a tongue and a nail are in close contact with each other to generate a vacuum, the infant experiences joy, warmth, satisfaction, and comfort without tension.

In this case, the bent holes 15 are formed at locations that are below the connection parts 14 and correspond to a first joint of the thumb 40, and a hole through which air may pass is not formed in an upper portion of the body 10.

That is, when an upper outer periphery surface of the body 10 is suctioned, the bent holes 15 are not inserted into a mouth, and thus the body 10 may be suctioned while forming a vacuum state. This allows the infant to partially experience joy, warmth, satisfaction, and comfort without tension, for example, like suctioning the thumb 40.

After the thumb suctioning prevention brace according to the inventive concept is worn, the body 10 may be suctioned instead of the thumb 40, and thus the infant feels some of the above experiences, but gradually loses interest because a suctioning target is not the thumb 40. Thus, the habit of suctioning the thumb 40 may be corrected.

Meanwhile, the body 10 has a plurality of fixing rings 17 having insertion holes 16 formed outside a lower portion thereof and is coupled to the band part 20.

In this case, the lower portion of the body 10 extends further from the first joint of the thumb 40 to cover a metacarpal bone of the thumb 40.

The band part 20 is coupled to the lower portion of the body 10 and is fixed to a wrist by connecting opposite ends thereof. That is, in a state in which the body 10 is worn in the thumb 40, the band part 20 is coupled to the body 10 and is fixed to the wrist so that the body 10 is not separated from the thumb 40.

The band part 20 includes a bendable intermediate band 21 inserted into the fixing rings 17, a fastener 22 formed at one end of the intermediate band 21 and forcibly fitted in the insertion holes 16, and a fastening band 24 extending from the other end of the intermediate band 21 and having a plurality of fastening holes 23 in which the fastener 22 is forcibly fitted.

In this case, the intermediate band 21 is fixed to the fixing rings 17 and is moved along the insertion holes 16. That is, when the fastener 22 is fastened to the fastening hole 23, as the intermediate band 21 is moved along the insertion holes 16, the fastener 22 and the fastening hole 23 may be selectively located at any one portion of a circumference of the wrist and may be fastened to each other. Even after the fastening, the intermediate band 21 may be moved, and thus more comfortable wearing may be provided.

Further, when the infant pulls the band part 20 or pushes the band part 20 against the floor or the like, as the intermediate band 21 is moved along the insertion holes 16, separation of the fastener 22 and the fastening holes 23 may be prevented, and a wearing state of the body 10 may be maintained.

Further, a protrusion 25 that may be caught on the fixing rings 17 without being inserted into the insertion holes 16 may be formed at an end of the fastening band 24, and an auxiliary hole 16 that is firstly and forcibly fitted before the fastener 22 is fastened to the fastening hole 23 and prevents the infant from easily loosening the band part 20 may be formed in the protrusion 25.

The detachable part 30 is provided inside the upper portion of the body 10, and a specific design 31 is displayed on an outer peripheral surface thereof.

In this case, the specific design 31 may include one or more of a character and a text and may be displayed with a printed matter or a sticker attached thereto.

Here, the body 10 is made of a transparent material, and the specific design 31 is exposed instead of a nail.

That is, while wearing the thumb suctioning prevention brace according to the inventive concept, the infant sees the specific design 31 instead of the nail of the thumb 40 while performing daily activities and sees the specific design 31 even when the infant acts to suction the thumb 40. As the specific design 31 is seen in this way, the specific design 31 is recognized.

In this case, as illustrated in FIG. 3, when the specific design 31 is a painful expression of a character, parents may tell a story that the character is painful when the thumb 40 is suctioned to the infant, allow the infant to recognize a result according to his/her behavior through the specific design 31, and thus expect and induce to stop suctioning the thumb 40.

Further, by replacing the detachable part 30 in which the design of a pleasant expression of a character is displayed as the specific design 31, the parents may also tell a story that the character is happy when the infant does not suction fingers to the infant.

Meanwhile, the detachable part 30 includes fitting bosses 32 fitted and coupled to the fitting holes 12 on opposite sides thereof and locking bosses 33 protruding outward from ends of the fitting bosses 32 and caught on the outer surface of the body 10. The outer peripheral surface of the detachable part 30 is in close contact with and is fixed to the contact groove 13.

That is, as the detachable part 30 is provided to be detachably attached to the contact groove 13 of the body 10, various detachable parts 30 on which various specific designs 31 are displayed may be replaced, the detachable part 30 allows the infant to visually recognize various character designs in addition to one character design, and thus the habit of suctioning the thumb 40 may be corrected more quickly.

Further, the locking bosses 33 may protrude long outward according to the character of the specific design 31, and the locking bosses 33 may prevent the body 10 from entering the mouth.

Further, when being fitted into the fitting holes 12, the fitting bosses 32 are coupled in close contact with each other so that air does not pass therebetween, and thus when the infant suctions the body 10, a vacuum state is formed and maintained so that the infant may feel some of the above experiences.

Further, the detachable part 30 has a concave groove 34 surrounding the nail, and a line 35 protrudes from an inner peripheral surface of the concave groove 34 in the lengthwise direction of the body 10.

Further, the line 35 spaces the nail apart from the concave groove 34, is provided as a plurality of lines 35 spaced apart from each other in a widthwise direction, and thus forms a passage 36 through which foreign substances may flow.

Meanwhile, since the thumb suctioning prevention brace of the inventive concept is formed of a silicone material, there is no problem at all even when the infant suctions the body 10, and since a silicone product may be sterilized and boiled, the product may be semi-permanently used without sanitary problems.

The effect of the inventive concept is to provide a thumb suctioning prevention brace in which a detachable part having a specific design displayed thereon is provided inside an upper portion of a body, the specific design instead of a nail of an infant is exposed through the transparent body, the infant is recognized that a thumb suctioning behavior is uncomfortable through the specific design, and thus a habit of suctioning a thumb may be corrected.

The effect of the inventive concept is to provide a thumb suctioning prevention brace in which the detachable part is attached to and detached from the body in an interchangeable manner, whereby various specific designs are recognized by the infant, and of course, the infant may be recognized not to suction the thumb by telling different stories according to the designs displayed on the detachable part.

The effect of the inventive concept is to provide a thumb suctioning prevention brace in which bent holes are formed in a middle part of the body to be long in a width direction and a plurality of connection parts are formed so that only a portion of a tip of the thumb is opened through an opening, whereby the thumb is supported by the connection parts when the infant bends the thumb, the bent holes are widened, and thus the infant may easily bend the thumb and easily grip an object.

Those skilled in the art to which the inventive concept pertains may understand that the inventive concept may be implemented in other specific forms without changing the technical spirit or essential features thereof. Therefore, it should be understood that the embodiments described above are illustrative but not limiting in all aspects. The scope of the inventive concept is indicated by the appended claims, which will be described below, rather than the detailed description, and the meaning and scope of the appended claims and all changes and modifications derived from equivalents thereof should be interpreted as being included in the scope of the inventive concept. In addition, an operation sequence of the components described in the above process should is not necessarily performed in a time series order, and even when the performance sequence of the configurations and operations is changed, when the subject matter of the inventive concept is satisfied, it is apparent that this process may belong to the scope of the inventive concept.

What is claimed is:

1. A thumb suctioning prevention brace comprising:
   a body configured to surround opposite sides, a back portion, and a nail of a thumb and having an opening configured to expose a bottom portion of the thumb;
   a band part coupled to a lower portion of the body and configured to be fixed to a wrist by connecting opposite ends thereof; and
   a detachable part provided inside an upper portion of the body, a specific design being displayed on an outer peripheral surface thereof,
   wherein the body is made of a transparent material and the specific design is exposed instead of the nail,
   wherein the body has fitting holes formed therein to pass through opposite sides of an upper portion thereof and has a contact groove which is inserted into an upper inner side thereof and with which the detachable part is in close contact, and
   wherein the detachable part includes fitting bosses fitted and coupled to the fitting holes on opposite sides thereof and locking bosses protruding outward from ends of the fitting bosses and caught on an outer surface of the body, and the outer peripheral surface of the detachable part is in close contact with and is fixed to the contact groove.

2. The thumb suctioning prevention brace of claim 1, wherein the body has one or more connection parts connecting opposite ends of the opening and a plurality of bent holes that pass long in a widthwise direction thereof and are formed in a lengthwise direction thereof,
   the connection parts are formed at locations corresponding to a tip of the thumb so that the thumb is not extracted through an upper portion of the opening, and
   when the thumb is bent, the tip of the thumb is supported by the connection parts, the bent holes are widened in a lengthwise direction thereof, and as the thumb is bent, the body is integrally bent.

3. The thumb suctioning prevention brace of claim 2, wherein the bent holes are formed at locations that are below the connection parts and correspond to a first joint of the thumb, and
   when an upper outer periphery surface of the body is suctioned, the bent holes are not inserted into a mouth, and thus the body is suctioned while forming a vacuum state.

4. The thumb suctioning prevention brace of claim 1, wherein the detachable part has a concave groove, and a line protrudes from an inner peripheral surface of the concave groove in a lengthwise direction of the body, and
   wherein the line is configured to space the nail apart from the concave groove, is provided as a plurality of lines spaced apart from each other in a widthwise direction thereof, and thus forms a passage through which foreign substances flow.

5. The thumb suctioning prevention brace of claim 1, wherein the body has a plurality of fixing rings having insertion holes formed outside a lower portion thereof,
   the band part includes a bendable intermediate band inserted into the fixing rings, a fastener formed at one end of the intermediate band and forcibly fitted in the insertion holes, and a fastening band extending from the other end of the intermediate band and having a plurality of fastening holes in which the fastener is forcibly fitted, and
   as the intermediate band is fixed to the fixing rings and is moved along the insertion holes, when the fastener is fastened to the fastening holes, the fastener and the fastening hole are configured to be selectively located and fastened in any one portion of a circumference of the wrist.

6. A thumb suctioning prevention brace comprising:
   a body configured to surround opposite sides, a back portion, and a nail of a thumb and having an opening configured to expose a bottom portion of the thumb;
   a band part coupled to a lower portion of the body and configured to be fixed to a wrist by connecting opposite ends thereof; and
   a detachable part provided inside an upper portion of the body, a specific design being displayed on an outer peripheral surface thereof,
   wherein the body is made of a transparent material and the specific design is exposed instead of the nail,
   wherein the body has one or more connection parts connecting opposite ends of the opening and a plurality of bent holes that pass long in a widthwise direction thereof and are formed in a lengthwise direction thereof,
   wherein the connection parts are formed at locations corresponding to a tip of the thumb so that the thumb is not extracted through an upper portion of the opening, and
   wherein when the thumb is bent, the tip of the thumb is supported by the connection parts, the bent holes are widened in a lengthwise direction thereof, and as the thumb is bent, the body is integrally bent.

7. The thumb suctioning prevention brace of claim 6, wherein the detachable part has a concave groove, and a line protrudes from an inner peripheral surface of the concave groove in a lengthwise direction of the body, and
wherein the line is configured to space the nail apart from the concave groove, is provided as a plurality of lines spaced apart from each other in a widthwise direction thereof, and thus forms a passage through which foreign substances flow.

8. The thumb suctioning prevention brace of claim 6, wherein the bent holes are formed at locations that are below the connection parts and correspond to a first joint of the thumb, and
wherein when an upper outer periphery surface of the body is suctioned, the bent holes are not inserted into a mouth, and thus the body is suctioned while forming a vacuum state.

9. The thumb suctioning prevention brace of claim 6, wherein the body has a plurality of fixing rings having insertion holes formed outside a lower portion thereof,
wherein the band part includes a bendable intermediate band inserted into the fixing rings, a fastener formed at one end of the intermediate band and forcibly fitted in the insertion holes, and a fastening band extending from the other end of the intermediate band and having a plurality of fastening holes in which the fastener is forcibly fitted, and
wherein as the intermediate band is fixed to the fixing rings and is moved along the insertion holes, when the fastener is fastened to the fastening holes, the fastener and the fastening hole are configured to be selectively located and fastened in any one portion of a circumference of the wrist.

10. A thumb suctioning prevention brace comprising:
a body configured to surround opposite sides, a back portion, and a nail of a thumb and having an opening configured to expose a bottom portion of the thumb;
a band part coupled to a lower portion of the body and configured to be fixed to a wrist by connecting opposite ends thereof; and
a detachable part provided inside an upper portion of the body, a specific design being displayed on an outer peripheral surface thereof,
wherein the body is made of a transparent material and the specific design is exposed instead of the nail,
wherein the detachable part has a concave groove, and a line protrudes from an inner peripheral surface of the concave groove in a lengthwise direction of the body, and
wherein the line is configured to space the nail apart from the concave groove, is provided as a plurality of lines spaced apart from each other in a widthwise direction thereof, and thus forms a passage through which foreign substances flow.

11. The thumb suctioning prevention brace of claim 10, wherein the body has a plurality of fixing rings having insertion holes formed outside a lower portion thereof,
wherein the band part includes a bendable intermediate band inserted into the fixing rings, a fastener formed at one end of the intermediate band and forcibly fitted in the insertion holes, and a fastening band extending from the other end of the intermediate band and having a plurality of fastening holes in which the fastener is forcibly fitted, and
wherein as the intermediate band is fixed to the fixing rings and is moved along the insertion holes, when the fastener is fastened to the fastening holes, the fastener and the fastening hole are configured to be selectively located and fastened in any one portion of a circumference of the wrist.

* * * * *